United States Patent [19]
Forsythe et al.

[11] Patent Number: 5,268,852
[45] Date of Patent: Dec. 7, 1993

[54] SELF DIAGNOSTIC PH SENSOR

[75] Inventors: Timothy J. Forsythe, Mission Viejo; Roland H. Koluvek, Orange, both of Calif.

[73] Assignee: Rosemount Analytical Inc., LaHabra, Calif.

[21] Appl. No.: 781,312

[22] Filed: Oct. 25, 1991

[51] Int. Cl.$^5$ ............... G06F 15/46; G01R 27/00
[52] U.S. Cl. .................. 364/482; 324/438; 364/486; 364/496; 364/550
[58] Field of Search ............ 364/482, 486, 571.01, 364/571.02, 571.04, 571.05, 550, 551.01, 496; 324/525, 723, 438, 439; 73/1 R, 1 H

[56] References Cited
U.S. PATENT DOCUMENTS

| | | | |
|---|---|---|---|
| 4,013,899 | 3/1977 | Guicheteall | 324/439 X |
| 4,536,274 | 8/1985 | Papadakis et al. | 324/438 X |
| 4,546,441 | 10/1985 | Burch | 364/482 |
| 4,777,444 | 10/1988 | Beijk et al. | 324/438 X |
| 4,829,253 | 5/9189 | Koluver | 324/438 |
| 4,998,068 | 3/1991 | McKee, Jr. | 324/438 |
| 5,046,028 | 9/1991 | Bryan et al. | 364/496 X |

Primary Examiner—Kevin J. Teska
Attorney, Agent, or Firm—Kinney & Lange

[57] ABSTRACT

An apparatus and method for measuring potentiometric electrode impedance for diagnostic purpose while continuously reading the results of the process value. A square wave is applied to an external circuit, which in turn is coupled to an electrode assembly output through a capacitor. The output of the electrode is converted into a pulse width modulated signal and sampled. These sampled values are used to calculate the impedance and process output value.

15 Claims, 2 Drawing Sheets

SELF DIAGNOSTIC PH SENSOR

BACKGROUND OF THE INVENTION

1. Field of Invention

This invention relates to an amplifier circuit for use with a sensor which requires only three wires for connection to a remote circuit. In particular, this invention allows for continuous process output measurement and continuous on line diagnosis of electrodes.

2. Description of Prior Art

Prior art systems such as the pH measuring system of U.S. Pat. No. 4,829,253, issued May 9, 1989, are capable of determining unknown values such as a voltage representation of the pH of a liquid and also of diagnosing electrode problems by checking the impedance of the sensor. The present invention allows for continuous on line measurement of both the process measurement and impedance.

The method used to determine sensor impedance in the prior art is also not as reliable or as accurate as the present invention's method. Prior art measures the decay time of the process output signal, or direct AC or DC impedance while the present invention measures area of the process signal output. This method provides for high accuracy measurement over the entire range for failed and functional electrodes.

Three wire pre-amplifier design is also known in the industry, but such design requires extensive bootstrap and bias circuitry for support. Not only have such systems involved unnecessary cost and complexity, the additional biasing circuitry requires more room and is less easily fitted into an electrochemical probe. Another major benefit of the present invention over the prior art is that the present invention does not require the use of a solution ground to reference the solution, thus reducing the number of electrodes needed, the size of the transmitter, and the cost.

SUMMARY OF THE INVENTION

The present invention provides a three wire amplifier circuit for use with a condition sensor, such as a pH sensor, to transmit to a remote circuit without using additional biasing circuitry. The pre-amplifier of the present system is compact and easily fitted into an electrochemical probe. The invention continuously measures a voltage representative of the on line process measurement and at the same time monitors sensor impedance using a square wave. The square wave is inputted to a remote circuit, and transmitted to a pH sensor probe over one of three wires. The other two wires array the "common" output of the system, and the voltage output of the preamplifier. The output is converted into a pulse width modulated signal by an inverter and sampled. The sampled values are used to calculate process output and impedance.

DETAILED DESCRIPTION OF THE PREFERRED EMBODIMENTS

Figure 1:
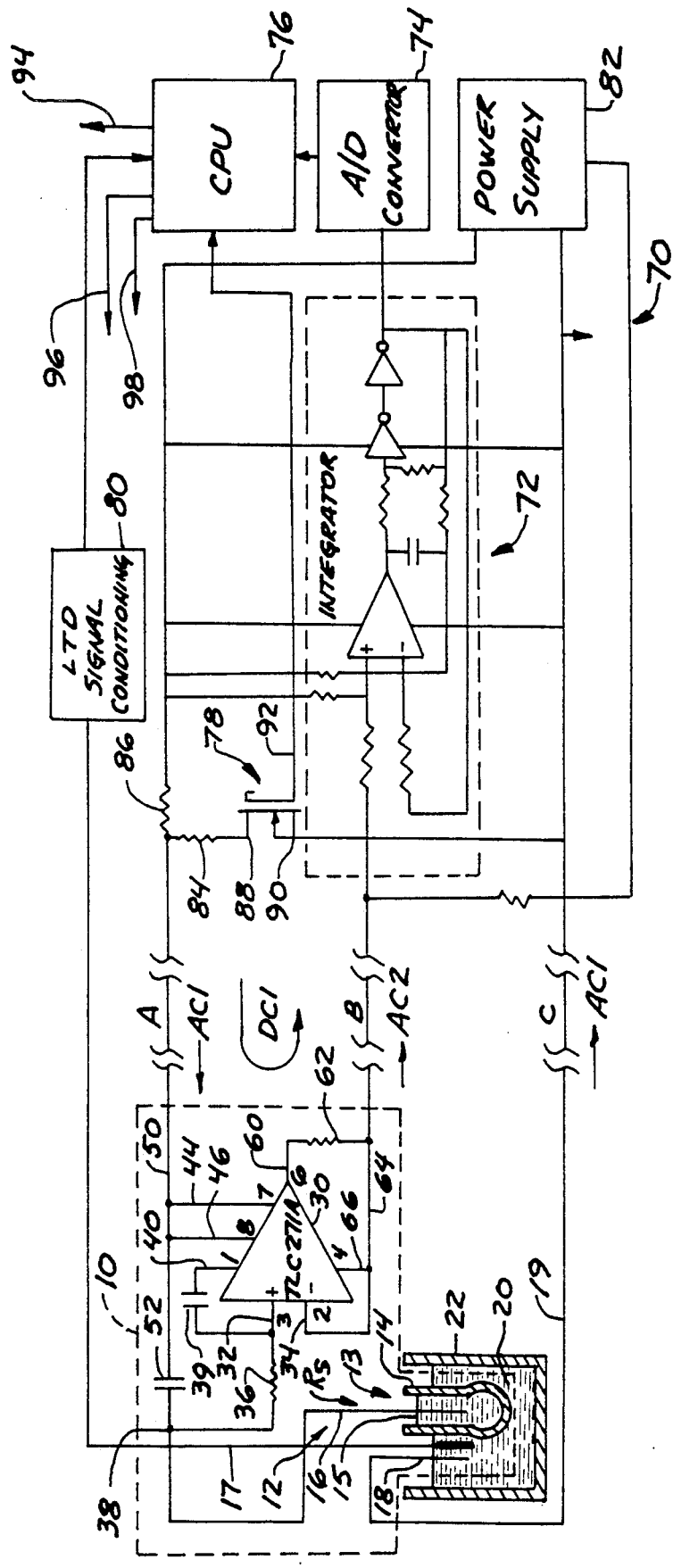
FIG. 1 is a schematic diagram of the three wire amplifier in combination with a pH sensing probe and an energization circuit.

In the FIGURE a transmitter 10 is shown in dashed lines containing a pH probe 12 which includes a pH electrode 13 comprising a glass container or cell 14 containing a known liquid 15 into which a conductor 16 is inserted and an electrode 1B which is inserted into a process fluid 20 whose pH is to be measured in a container 22. Process fluid also contains a temperature probe 17. Electrode 18 is shown only schematically and normally includes a salt bridge as is known in the art. These probes operate to develop a voltage $e_s$ between the conductor 16 and the electrode 18 which varies as a function of the pH of the liquid 20.

Electrode 18 is shown connected to a line 19 identified by the letter "C" which constitutes the "common" output of the system and is one of the three wires to the transmitter 10. Conductor 16 is used for providing the output signals to the circuit and is connected to a junction point 38. The resistance of the pH electrode 13 is represented by $R_s$. This value will change when the glass cell becomes coated, cracked, or broken.

An amplifier 30 which is, for example, an operational amplifier of the type TLC 271A made by Texas Instruments is shown in the figure and has a high impedance, non-inverting or positive input 32 and an inverting or negative input 34. The non-inverting input 32 is shown connected through a resistor 36 to the junction point 38 to which the conductor 16 is also connected. The signal from the conductor 16 is thus coupled through resistor 36 to the non-inverting input of amplifier 30. Resistor 36 in the preferred embodiment has a resistance of approximately 10K ohms. It is seen that the signal from conductor 16, which is related to the unknown voltage $e_s$ is presented to the non-inverting input of the operational amplifier 30. A capacitor 39 is shown connected between the non-inverting input 32 and the offset terminal 40 for purpose of providing of bypass and amplifier stability, as shown.

A positive supply terminal 44 and a bias select terminal 46 are connected together to a conductor 50 which is identified by the letter "A" conductor 50, is the conductor for the positive side of the power supply to the system and is another of the three wires to the transmitter 10.

Conductor 50 is also connected through a capacitor 52 to the junction point 38 for purposes of providing a square wave for use in checking the electrode 13 as will be described hereinafter. In the preferred embodiment capacitor 52 is approximately 1 nanofarad. The transmitter 10 operates as a preamplifier and is usually mounted as close to the electrode 13 as possible. In use, the electrode 13, electrode 18, and the preamplifier all are mounted on a signal probe package 12, with the transmitter mounted at the head of the probe.

The output of amplifier 30 is on a conductor 60 and is shown connected through a resistor 62 to a conductor 64 which is also identified by the letter "B", and is the other of the three wires to the transmitter 10. Conductor 64 is connected directly to the inverting input 34 and to the negative supply terminal 66 of amplifier 30. Thus, the output of the amplifier 30 which, as connected, will closely follow the non-inverting input on conductor 32, is connected by a resistor 62 not only to the inverting input 34 but also to the negative supply terminal 66. By this connection, the output of the operational amplifier 30 drives the negative power supply and the circuit output becomes a negative power supply. Thus the voltage output of the transmitter will appear on the conductor "B".

The transmitter 10 is usually located right on the probe 12, remote from the source of power and further signal conditioning circuits. Conductors which supply the power supply inputs and the output are shown by the broken line connectors "A", "B", and "C", which lead from the transmitter 10 to a remote circuit 70.

Remote circuit 70 comprises an integrator 72 connected to an analog to digital converter 74, which is coupled to a microprocessor (CPU) 76. The CPU 76 is connected to a MOSFET 78, and a RTD signal conditioner 80. The integrator 72 is connected to a power supply 82. The MOSFET 78 is coupled to a voltage divider network 84, 86 at its source 88, conductor C at its drain 90, and the CPU 76 at its gate 92. Conductor B is connected directly to the integrator 72, which is connected to the analog to digital converter 74. The RTD signal conditioner 80 is connected to a temperature probe 17 in the liquid 20, and is coupled to the CPU 76. The CPU also provides a process output on line 94, impedance output on line 96, and error or fault signals on line 98.

In operation, a square wave is applied from the CPU 76 to the gate 92 of the MOSFET 78 resulting in a step voltage through the capacitor 52 and onto the process electrode's output on conductor 16. By applying a square wave, a nonpolarized electrode may be maintained resulting in no interference of the electrodes average output. A near perfectly symmetrical square wave of positive and negative pulses is maintained by using the voltage divider network 84, 86. This near perfect symmetry allows the ability to sample the electrode 13 output and use this sample to obtain both sensor impedance and process output readings, by calculation methods described hereinafter.

As the pH of fluid 20 changes, the voltage $e_s$ will change and accordingly the voltage to the noninverting input 32 of amplifier 30 will change. Because of the feedback system through resistor 62 and conductor 64, the voltage at the inverting input 34 of amplifier 30 will follow the change and the magnitude of the voltage signal on conductor B will change accordingly. The signal on conductor B is input into the integrator circuit 72 whose pulse width modulated output is then sent to the A to D converter 74 to convert the signal into a digital signal for input to the CPU 76. Both the process output and impedance is obtained by measuring the on-time of the positive and negative pulses and the total time of the positive and negative pulses of the pulse width modulated signal. The on-times and total-times are accumulated for a given period of time (T). This provides information for determining the area under the decay curve (FIG. 2) using the basic formula:

$$E_t = E_o e_s^{-t/RC}$$

The area equation can be derived by integration and is obtained at the output of the integrator. It can be shown that at $t=T$ $$R = \frac{AREA}{C(E_o - E_T)}$$

and at $T = \text{infinity}$, $$R = \frac{AREA}{E_o C}$$

Figure 2:
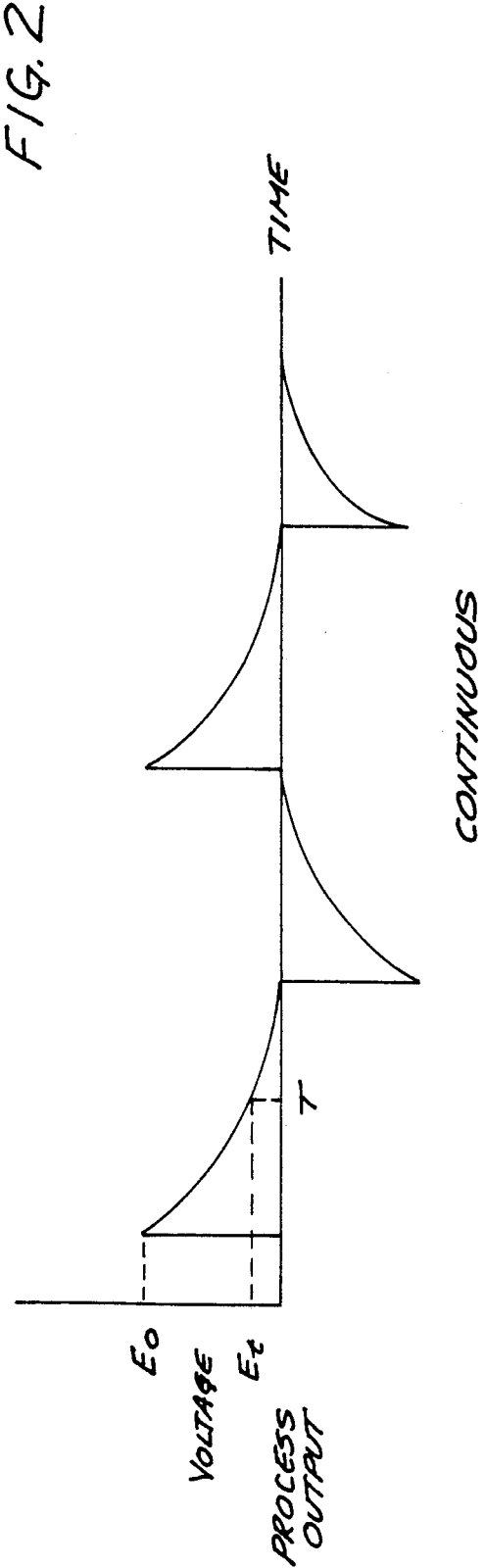
FIG. 2 is a schematic representation of a wave form obtained.

Where:
T = measurement period
t = time variable
$E_t$ = voltage at time T
$E_o$ = step voltage (FIG. 2)
R = impedance
C = capacitance (52)
$e_s$ = electrode output
$E_T$ = voltage at time "T" (FIG. 2)

The process output is obtained by determining the ratio of the on-time to the total-time of the positive and negative pulses of the pulse width modulated signal from the integrator, and averaging them. Due to the symmetry of the pulses, the average of these ratios is the DC baseline equivalent to the process output. The impedance output is obtained similarly, but by subtracting the two ratios and averaging them. This removes the DC baseline offset and leaves a signal indicating only the area under the decay curve, which in turn provides an accurate indication of impedance as indicated above.

Very large impedances have very long decay times. The period of the square wave may not be long enough to allow the output to decay to its prestep value (DC baseline in FIG. 2) before the next step occurs. This leads to errors in the impedance readings. The readings can be corrected by capturing the voltage level when the last area segment is sampled ($E_t$) and using the basic formula above. The following equations express the relationships:

$$\text{Process Output} = \frac{\frac{SU1}{SUT} + \frac{SD1}{SDT}}{2} \cdot P_c + P_{offset}$$

$$Z_u = \text{Impedance} = \frac{\frac{SU1}{SUT} - \frac{SD1}{SDT}}{2} \cdot Z_c + Z_{offset}$$

Where:
SU1 = on-time of positive pulse
SUT = total-time of positive pulse
SD1 = on-time of negative pulse
SDT = total time of the negative pulse
$P_c$ = spanning constant for process calibration
$P_{offset}$ = zero offset for process calibration
$Z_c$ = spanning constant for impedance calibration
$Z_{offset}$ = zero offset for impedance calibration
$Z_u$ = uncompensated impedance The impedance is further corrected for temperature errors by the following formula:

$$Z_t = \frac{Z_u}{(2^{1/D})(T - T_{ref})}$$

Where:
$Z_t$ = temperature corrected impedance
$Z_u$ = uncompensated impedance
D = doubling constant
T = process temperature
Tref = reference temperature In the following equation, $P_c$ and $Z_c$ and the offsets from zero are derived factors determined from standard calibration procedures. The procedure for determining the quantity is the same for both process output calibration and impedance calibration. The calibrator inputs both a low and a high process value, and records in the computer the "actual" values inputted from the output signal. The high and low actual values (A) and the high and low measured values (M) are then used to calculate the span and offset values for the process. The process calculations are shown below. The impedance calculations are identical:

$$P_{offset} = \frac{A_L(M_H - P_{offset}) + A_H(P_{offset} - M_L)}{(M_H - M_L)}$$

$$P_c = \text{Spanning Constant} = \frac{P_c(A_H - A_L)}{(M_H - M_L)}$$

Where:
- $A_L$ = actual low value
- $A_H$ = actual high value
- $M_L$ = measure low value
- $M_H$ = measure high value The doubling constant, D, represents the change in temperature which results in a doubling of electrode impedance. For example if D=8, the electrode impedance doubles every 8 degrees C with reference to Tref. As the temperature increases the impedance decreases. The value D=8 is used for electrode impedances in the form of the invention.

Using the above equations for determining impedance, accurate detection of aged or coated electrodes is possible. Coated and aging electrode impedances slowly rise over a period of time. In this embodiment the user enters a maximum allowable impedance value, which may vary depending upon the type of electrode and the process in which the electrode is immersed. When the value entered is reached by the measured value, a fault indicator informs the user that replacement, maintenance, and/or recalibration is necessary.

A cracked electrode is indicated by a sharp decrease in electrode impedance. The user enters a set point impedance value equivalent to the amount of error (decrease in impedance) to be allowed in percentage, which would indicate a cracked electrode. This method works by using the following filtering equation with two different values for the filter constant.

$$Z_f = Z_t - \frac{(Z_t - Z_u)}{F}$$

Where:
- $Z_f$ = filtered impedance
- $Z_u$ = uncompensated impedance
- $Z_t$ = temperature corrected impedance
- F = filter constant The filter values are functions of time, which represent response time by the system. By using two different values of the filter constant, a trend of the upward or downward shifts of impedances is maintained. The larger filter constant corresponds to a slower response of the system, where the smaller filter constant corresponds to a faster response time.

When the impedance of the system changes, the $Z_f$ (fast) with the faster or smaller filter constant will change faster than $Z_f$(slow) with the large or slow filter constant. If the difference between the two values of $Z_f$ exceeds a predefined value, 10% for example, a timer is started, and the value of $Z_f$(slow) with the larger filter constant is stored for reference. At some user defined period of time later, the difference between $Z_f$ (fast) with small filter constant and $Z_f$(slow) that was stored is calculated. If this difference value exceeds a user preset value of error, it is known a cracked electrode exists, and an error signal is generated. The timer is used to prevent a stray noise signal from generating an error. By comparing $Z_s$ (fast) and the same $Z_f$(slow), at some period of time apart, the chances of stray noises causing faults are greatly reduced. This is illustrated by the flow chart of FIG. 3.

Figure 3:
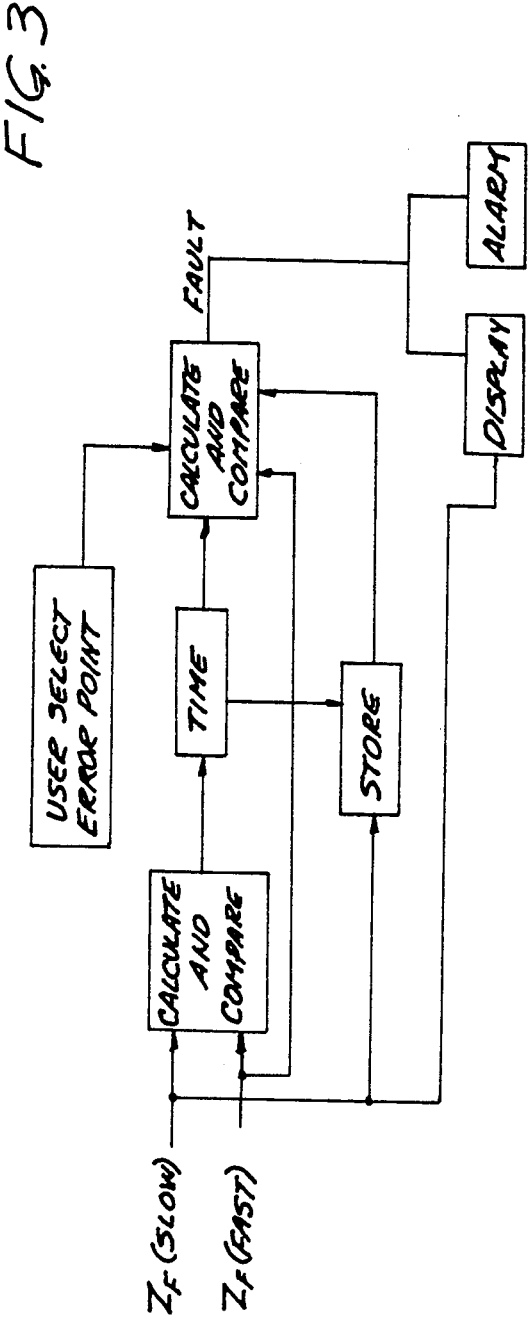
FIG. 3 is a simplified flow chart which illustrates the determination of unwanted impedance change in an electrode.

The fault signal of FIG. 3, which indicates an impedance variation, can be used to drive a display or to operate a relay to provide an alarm. The fault signal can be set to be provided as a prediction of failure, to give an alarm, or indicate when an electrode should be replaced. The signal can be to indicate when the electrode impedance exceeds a user selected value indicating an old or coated electrode, or when the impedance falls below a selected value indicating a cracked electrode.

Failed electrodes are indicated by either very high or very low impedances. The procedure allows the user to enter maximum and minimum impedance values for fault purposes. If the impedance values exceed these limits, fault signals are generated.

Coated and aging electrodes' impedances slowly rise over a period of time. This procedure stores the nominal impedance value each time a calibration is performed. The user enters a value equivalent to the amount of error in percentage before calibration is needed. These values may vary depending on the type of electrode and the process in which the electrode is immersed. When the value entered is reached, a fault indicator informs the user that replacement, maintenance and/or recalibration is necessary.

The apparatus is shown with a pH sensor, but can be adapted for indications of impedances of electrodes of general use chemical sensors such as sensors for sensing sodium or potassium.

Although the present invention has been described with reference to preferred embodiments, workers skilled in the art will recognize that changes may be made in form and detail without departing from the spirit and scope of the invention.

What is claimed is:

1. An apparatus for measuring potentiometric electrode impedances for diagnostic purposes while continuously providing a process output indicating a parameter of a fluid comprising:
   microprocessor means for applying a continuous square wave to a remote circuit;
   a first electrode contacting a fluid of known characteristics;
   a second electrode contacting the fluid, the potential between the first and second electrodes comprising symmetrical positive and negative pulses and being indicative of the process output; amplifier means having an input connected to the first electrode for amplifying the process output;
   integrator means coupled to integrate the process output after the process output has been amplified by the amplifier means;
   means coupling the output of integrator means to the microprocessor; and
   means in the microprocessor for providing an indication of the impedance between the electrodes as a function of the integrator means output.

2. The apparatus of claim 1 wherein the means in the microprocessor provides an output representative of the impedance according to the formula:

$$Z_u = \text{Impedance} = \left( \frac{\frac{SU1}{SUT} - \frac{SD1}{SDT}}{2} \right) \cdot Z_c + Z_{offset}$$

Where
SU1 = on-time of positive pulse
SUT = total-time of positive pulse
SD1 = on-time of negative pulse
SDT = total time of negative pulse
$Z_c$ = spanning constant for impedance calibration
Z offset = zero offset for impedance calibration
$Z_u$ = uncompensated impedance.

3. The apparatus of claim 1 wherein the microprocessor includes additional means for providing an output representative of the process output according to the formula:

$$P_{out} = \text{Process Output} = \left( \frac{\frac{SU1}{SUT} + \frac{SD1}{SDT}}{2} \right) \cdot P_c + P_{offset}$$

Where
SU1 = on-time of positive pulse
SUT = total-time of positive pulse
SD1 = on-time of negative pulse
SDT = total time of negative pulse
$P_c$ = spanning constant for process calibration
P offset = zero offset for impedance calibration 4. The apparatus of claim 1 wherein the second electrode contacting the fluid is a reference electrode with a salt bridge making electrode contact to the process fluid.

5. The apparatus of claim 1 wherein electrode impedance is calculated simultaneously with the process output, and error means in the microprocessor to detect electrode impedance error relative to a reference, and provide the error as a fault signal.

6. An apparatus for measuring potentiometric electrode impedances for diagnostic purposes while continuously reading the results of a desired process parameter comprising:
means for applying a continuous square wave to a remote circuit;
electrode means coupled to the remote circuit for determining a property of a fluid and for providing an electrical output indicative of the property, the output being a pulse symmetrical square wave relative to a reference line;
integrator means coupled to receive the output; and
an analog to digital converter coupled to the output of the integrator means and to a microprocessor, the microprocessor providing an indication of impedance between the electrodes as a function of an area under the symmetrical pulses for a relative time.

7. An apparatus for measuring electrode impedance for diagnostic purposes while continuously reading an output for a parameter measured by the electrodes comprising:
means for applying a square wave to a remote circuit;
electrode means coupled to the remote circuit for determining a parameter of a fluid and for providing an electrical potential process output indicative of the parameter, the process output being a square wave symmetrical relative to a reference level;
integrator means coupled to receive the process output; and
a microprocessor coupled to the output of the integrator means, and means in the microprocessor for providing an indication of impedance between the electrodes as a function of an area under the symmetrical square wave process output signal during a selected time period.

8. The apparatus of claim 7 wherein the means for calculating includes means for storing the filtered impedance when the difference in the filtered impedances exceeds a range of 10%.

9. The apparatus of claim 7 wherein the process output is a series of negative and positive pulses during the selected time period, and wherein the means in the microprocessor provides the indication of impedance between the electrodes as an impedance signal on a continuous basis, and further comprising:
first and second filter means for separately filtering having a filter signal, one of said filter means having a filter constant slower than the filter constant of the other filter means;
means for calculating differences in the filtered impedance signal values from the first and second filter means, respectively, after filtering and for determining when a difference in the filtered values exceeds a preselected error, and for then storing the filtered value of the impedance from the one filter means; and
means for calculating differences in the filtered impedance signal from the other filter means and the stored filter impedance value of the one filter means after a preselected period of time, and for providing an output signal indicating a greater than desired change in impedance if the last mentioned calculated difference exceeds a preselected amount.

10. The apparatus of claim 9 wherein a signal is generated when the output signal indicates an electrode impedance below a user selectable value thereby indicating a cracked electrode.

11. The apparatus of claim 9 wherein a signal is provided when the change in impedance indicates an electrode impedance greater than a user selected value.

12. A method for measuring potentiometric electrode impedances for diagnostic purpose while continuously providing a parameter indicating signal from a process material comprising:
inputting a symmetrical continuous square wave signal to a remote circuit;
applying the square wave to a second circuit containing an electrode which receives the symmetrical signal;
converting an electrode output of the electrode receiving the symmetrical signal by integration to obtain a pulse width modulated signal;
sampling the pulse width modulated signal;
measuring on-time and a selected total time of the pulse width modulated signal; and
selectively calculating the impedance of the electrode and a parameter indicating signal from the converted electrode output.

13. The method of claim 12 wherein said pulse width modulated signal comprises positive pulses and negative pulses, each having on time and off time and wherein the calculating step comprises applying the following formula:

$$Z_u = \left( \frac{\frac{SU1}{SUT} - \frac{SD1}{SDT}}{2} \right) * Z_c + Z_{offset}$$

Where

SU1 = on-time of positive pulse

SUT = total-time of positive pulse

SD1 = on-time negative pulse

SDT = total time of negative pulse $Z_C$: Spanning constant for $Z_u$ = uncompensated impedance Z offset = Zero offset for impedance calibration.

14. The method of claim 13 including the step of applying a correction formula:

$$Z_t = \frac{Z_u}{(2^{1/D})(T-Tref)}$$

Where:

$Z_t$ = temperature corrected impedance $Z_u$ = uncompensated impedance

D = doubling constant

T = process temperature

Tref. = reference Temperature.

15. The method of claim 12 including the steps of:

providing the indication of impedance as an impedance signal;

the further steps of separately filtering the impedance through a fast filter and a slow filter to provide a fast filter impedance and a slow filter impedance;

determining the difference between the slow filter impedance and the fast filter impedance, and storing the fast filter impedance when such difference exceeds a preselected amount, subsequently determining a second difference between the slow filter impedance and the stored fast filter impedance; and providing a signal if the subsequently determined difference exceeds a selected amount.

* * * * *

UNITED STATES PATENT AND TRADEMARK OFFICE
CERTIFICATE OF CORRECTION

PATENT NO.   : 5,268,852
DATED        : December 7, 1993
INVENTOR(S)  : Forsythe et al.

It is certified that error appears in the above-indentified patent and that said Letters Patent is hereby corrected as shown below:

Column 1, line 54, cancel "array" and insert --carry--.

Column 2, line 8, cancel "1B" and insert --18--.

Column 7, line 12, cancel "total-time" and insert --total time--;

Column 7, line 61, cancel "impedance" and insert --impedances--.

Column 8, line 22, cancel "having a filter" and insert --the impedance--;

Column 8, line 34, cancel "filter" and insert --filtered--.

Column 9, line 18, add --impedance calibration--.

Signed and Sealed this

Thirtieth Day of August, 1994

Attest:

BRUCE LEHMAN

Attesting Officer *Commissioner of Patents and Trademarks*